(12) United States Patent
Dubois et al.

(10) Patent No.: US 8,243,280 B2
(45) Date of Patent: Aug. 14, 2012

(54) LASER ULTRASONIC MEASUREMENT SYSTEM WITH MOVABLE BEAM DELIVERY

(75) Inventors: Marc Dubois, Keller, TX (US); Thomas E. Drake, Fort Worth, TX (US); Marvin Klein, Pacific Palisades, CA (US)

(73) Assignee: iPhoton Solutions, LLC, Ft. Worth, TX (US)

( * ) Notice: Subject to any disclaimer, the term of this patent is extended or adjusted under 35 U.S.C. 154(b) by 378 days.

(21) Appl. No.: 12/464,571

(22) Filed: May 12, 2009

(65) Prior Publication Data

US 2009/0290163 A1 Nov. 26, 2009

Related U.S. Application Data

(60) Provisional application No. 61/054,801, filed on May 20, 2008.

(51) Int. Cl.
*G01B 11/02* (2006.01)
(52) U.S. Cl. ........................................ 356/502
(58) Field of Classification Search .................. 356/502; 73/622, 865.8
See application file for complete search history.

(56) References Cited

U.S. PATENT DOCUMENTS

| | | |
|---|---|---|
| 5,585,921 A | 12/1996 | Pepper et al. |
| 6,057,927 A | 5/2000 | Levesque |
| 6,094,447 A | 7/2000 | Drake |
| 6,122,060 A | 9/2000 | Drake |
| 6,176,135 B1 | 1/2001 | Dubois |
| 6,335,943 B1 * | 1/2002 | Lorraine et al. ............... 372/28 |
| 6,378,387 B1 | 4/2002 | Froom |
| 6,483,859 B1 | 11/2002 | Drake |
| 6,571,633 B1 | 6/2003 | Drake |
| 6,606,909 B2 | 8/2003 | Dubois |
| 6,633,384 B1 | 10/2003 | Drake, Jr. et al. |
| 6,637,266 B1 | 10/2003 | Froom |

(Continued)

FOREIGN PATENT DOCUMENTS

WO WO 2008103209 8/2008

OTHER PUBLICATIONS

Drake, Thomas E. et al., "AFRL-ML-WP-TR-1998-4128: Large Area Composite Inspection System (Final Report for Period Oct. 1992-Jun. 1998)," Air Force Research Laboratory, Jun. 1998.

(Continued)

*Primary Examiner* — Tarifur Chowdhury
*Assistant Examiner* — Jonathon Cook
(74) *Attorney, Agent, or Firm* — Kelly J. Kubasta; Klemchuk Kubasta LLP

(57) ABSTRACT

A laser ultrasonic measurement system includes a first and a second laser source configured to generate a first and a second laser beam, respectively. A movable mechanical link is arranged to transmit the first laser beam. The movable mechanical link is formed by a plurality of rigid sections interconnected by rotating joints. A robot is configured to support and control the movement of at least a section of the mechanical link to transmit the first laser beam to an object. An optical scanner is positioned proximate to the mechanical link. The optical scanner is configured to direct the first and second laser beams onto the object. An interferometer is optically coupled to the optical scanner. The interferometer is configured to receive reflected light from the object and in response generate an electrical signal. The first laser source is kinematically mounted in a housing assembly.

12 Claims, 7 Drawing Sheets

U.S. PATENT DOCUMENTS

| | | |
|---|---|---|
| 6,643,002 B2 | 11/2003 | Drake |
| 6,649,900 B2 | 11/2003 | Filkins |
| 6,657,733 B1 | 12/2003 | Drake |
| 6,668,654 B2 | 12/2003 | Dubois |
| 6,684,701 B2 | 2/2004 | Dubois |
| 6,711,954 B2 | 3/2004 | Drake |
| 6,732,587 B2 | 5/2004 | Lorraine |
| 6,856,918 B2 | 2/2005 | Dubois |
| 7,038,790 B2 | 5/2006 | Drake |
| 7,117,134 B2 | 10/2006 | Dubois |
| 7,208,749 B2 | 4/2007 | Drake |
| 7,286,241 B2 | 10/2007 | Drake |
| 7,342,665 B2 | 3/2008 | Drake |
| 7,369,250 B2 | 5/2008 | Dubois |
| 7,370,532 B2 | 5/2008 | Osterkamp |
| 7,463,363 B2 | 12/2008 | Drake |
| 7,474,411 B2 | 1/2009 | Dubois |
| 7,480,574 B2 | 1/2009 | Dubois |
| 7,545,509 B2 | 6/2009 | Drake |
| 7,561,281 B2 | 7/2009 | Drake |
| 7,576,848 B2 | 8/2009 | Dubois |
| 7,605,924 B2 | 10/2009 | Howard |
| 7,612,890 B2 | 11/2009 | Drake |
| 7,612,894 B2 | 11/2009 | Drake |
| 7,667,851 B2 | 2/2010 | Dubois |
| 7,684,047 B2 | 3/2010 | Drake |
| 7,784,348 B2 | 8/2010 | Dubois |
| 7,791,739 B2 | 9/2010 | Dubois |
| 7,800,762 B2 | 9/2010 | Deaton |
| 2002/0186380 A1 | 12/2002 | Drake, Jr. |
| 2004/0027578 A1 | 2/2004 | Drake, Jr. et al. |
| 2004/0154402 A1 | 8/2004 | Drake |
| 2005/0120803 A1 | 6/2005 | Sokol et al. |
| 2005/0231735 A1 | 10/2005 | Dubois |
| 2006/0132804 A1 | 6/2006 | Dubois |
| 2007/0002319 A1* | 1/2007 | Knopp et al. .......... 356/301 |
| 2008/0181268 A1 | 7/2008 | Dubois |
| 2008/0291465 A1 | 11/2008 | Lorraine |
| 2008/0291963 A1 | 11/2008 | Deaton |
| 2009/0010285 A1 | 1/2009 | Dubois |
| 2010/0277723 A1* | 11/2010 | Rezac et al. .......... 356/301 |

OTHER PUBLICATIONS

Drake, Tommy, et al., "LaserUT Technology Development Programs for the Ultrasonic Inspection of Composites in the Aerospace Industry," Lockheed Martin Aeronautics, Jul. 25, 2007.

Dubois, Marc, et al., "LaserUT Technology Development Programs for the Ultrasonic Inspection of Composites in the Aerospace Industry," Preprint of Review of the QNDE, Jul. 2007.

Dubois, Marc, et al., "Low-Cost Ultrasonic Inspection of Composites for Aerospace Applications with LaserUT Technology," Preprint from Journal of Japanese Society of Non-Destructive Inspection, 2008.

Dubois, Marc, et al., "Low-Cost Ultrasonic Inspection of Composites for Aerospace Applications with LaserUT Technology," (Review Paper), Recent Progress in Laser-Ultrasonics 1, 2008.

Monchalin, Jean-Pierre, "Laser-Ultrasonics: From the Laboratory to the Shop Floor," Advanced Performance Materials 5,7-23, Kluwer Academic Publishers, 1998.

Nelson, James M., et al., "AFRL-ML-WP-TR-1998-4127: Enhanced Laser Generated Ultrasound (Final Report for Dec. 1996 through Feb. 1998)," Air Force Research Laboratory, Jul. 8, 1998.

Romer Hexagon Metrology, "Romer Portable Coordinate Measurement Systems," InnovMetric Software, Inc., May 2008.

Supplementary European Search Report and the European Search Opinion date Feb. 22, 2012 for corresponding EP patent application No. EP 09751203.2. 6 pgs.

* cited by examiner

LASER ULTRASONIC MEASUREMENT SYSTEM WITH MOVABLE BEAM DELIVERY

CROSS-REFERENCE TO RELATED APPLICATIONS

Pursuant to 35 U.S.C. §119(e), this application claims priority from, and hereby incorporates by reference for all purposes, U.S. Provisional Patent Application Ser. No. 61/054,801, entitled IMPROVED LASER-ULTRASONIC INSPECTION OF COMPLEX PARTS USING AN ARTICULATED BEAM DELIVERY SYSTEM, and filed May 20, 2008.

FIELD OF THE INVENTION

The invention generally relates to laser ultrasonic measurement, and more particularly to a laser ultrasonic measurement system with movable beam delivery.

BACKGROUND OF THE INVENTION

Laser ultrasonic measurement systems are frequently used for structural analysis of parts and components. These systems offer advantages over non-laser type systems (e.g., piezoelectric transducer-based systems). Laser ultrasonic systems are typically non-contact systems that test a structure by measuring ultrasonic waves induced in a structure. Typically, a first laser beam, referred to as a generation beam, is directed to a structure causing thermal expansion of the structure, which generates ultrasonic waves. A second laser beam, referred to as a detection beam, is used to illuminate the structure. Reflected light from the structure is processed for analysis of the structure.

Laser ultrasonic systems are well suited for many industrial applications, such as measurement of steel at high temperature, measurement of paint thickness and non-destructive testing of complex structures.

One drawback of existing laser ultrasonic measurement systems is the difficulty of delivering the generation and detection beams to a structure or a part that may not be easily accessible. Since existing systems are not easily movable, delivery of the generation and detection beams to a structure that is not easily accessible can be challenging. The generation beam, in particular, may be difficult to deliver to such a structure because its wavelength may preclude delivery via a fiber optic cable. Also, large peak power or large average power of the generation beam increases the difficulty of delivery to the structure.

SUMMARY

In one embodiment, a laser ultrasonic measurement system includes a first and a second laser source configured to generate a first and a second laser beam, respectively. A movable mechanical link is arranged to transmit the first laser beam. The mechanical link is formed by a plurality of rigid sections interconnected by rotating joints. In one implementation, at least two reflecting mirrors are arranged in the joint to transfer the first laser beam between adjacent rigid sections.

A robot is configured to support and control the movement of at least a section of the mechanical link. The robot enables the mechanical link to transmit the first laser beam to an object. An optical scanner is positioned proximate to the mechanical link. The optical scanner directs the first and second laser beams onto the object. The optical scanner is mounted on a rotating axis. An interferometer is optically coupled to the optical scanner. The interferometer is configured to receive reflected light from the object and in response generate an electrical signal.

In one embodiment, the second laser beam is transmitted proximate to the optical scanner by an optical link. The first laser source is kinematically mounted in a housing assembly by a plurality of supports to isolate the laser source from stress.

The robot is configured to provide displacement to the mechanical link for translational and rotational movements of the optical scanner proximate to the mechanical link. The robot includes a robotic arm configured to support and control the movement of the mechanical link for translational and rotational movements of the optical scanner proximate to the mechanical link.

BRIEF DESCRIPTION OF THE DRAWINGS

For a more complete understanding of the features, example embodiments and possible advantages of the present invention, reference is now made to the detailed description of the invention along with the accompanying figures and in which.

DETAILED DESCRIPTION OF THE INVENTION

Figure 1:
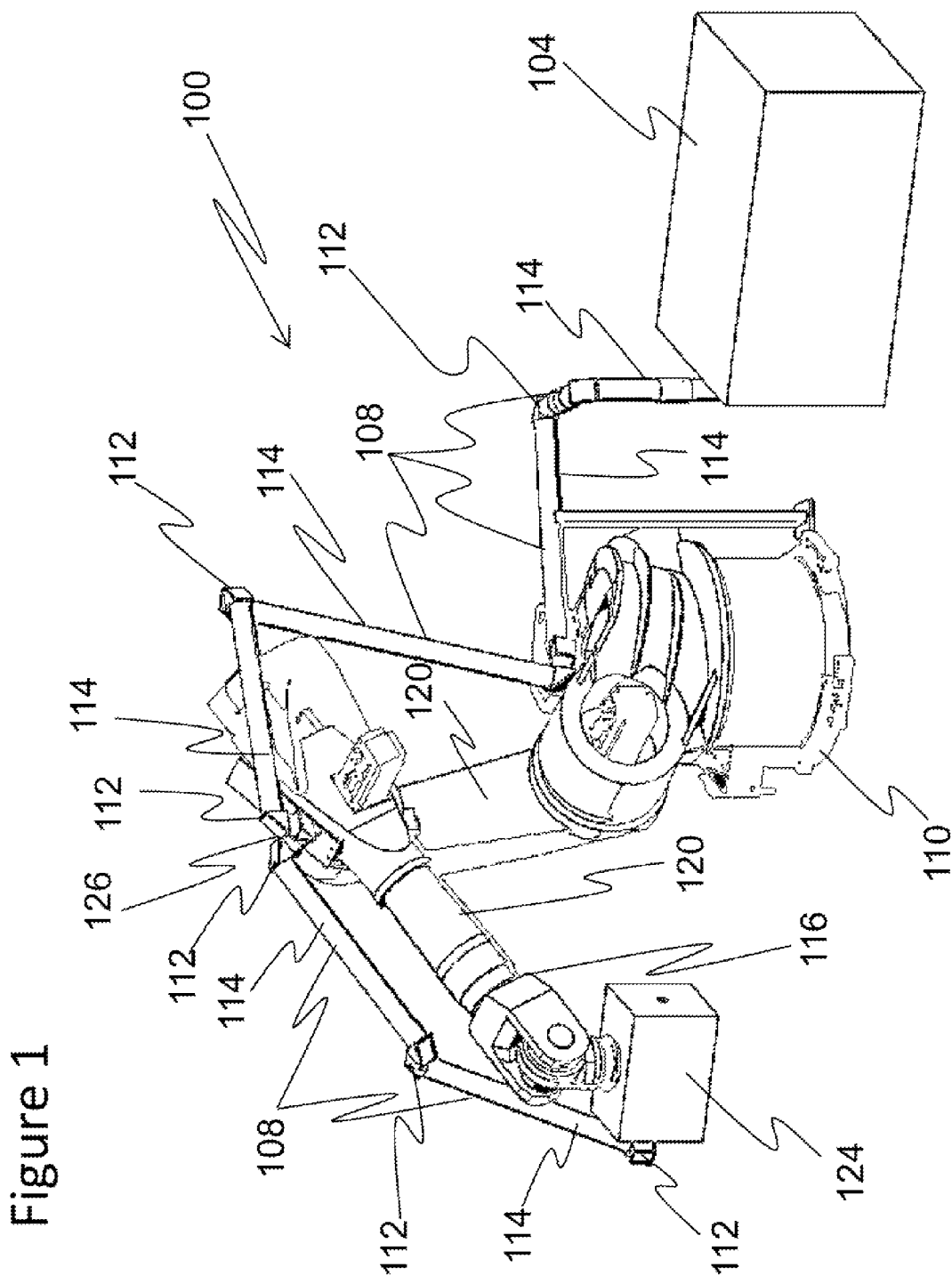
FIG. 1 illustrates a laser ultrasonic measurement system in accordance with an embodiment.

FIG. 1 illustrates a laser ultrasonic measurement system 100 in accordance with an embodiment. The system 100 includes a laser source 104 that generates a laser beam (not shown in FIG. 1). Although the system 100 is illustrated as having only a single laser source, it will be appreciated that the system 100 may be implemented with two or more laser sources, each configured to generate a laser beam. The system 100 includes a movable mechanical link 108 coupled to the laser source 104. The movable mechanical link 108 is configured to transmit the laser beam from the laser source 104 to a desired location or an object. The laser beam, for example, may be directed to a part or a component that is being analyzed. The mechanical link 108 may be configured to transmit multiple laser beams, each originating from an independent laser source.

The system 100 includes a robot 110 configured to support and control the movement of at least a section of the mechanical link 108. In one implementation, the robot 110 may include a robotic arm 116 to support and guide the mechanical link 108. It will be apparent to those skilled in the art that the system 100 may be implemented with a robot without the robotic arm.

The robotic arm 116 provides mobility to the system 100 by guiding the mechanical link 108 proximate to the part or component being tested. In one implementation, the mechanical link 108 is formed by a plurality of link sections 114 interconnected by joints 112. The joints 112 may, for example, be rotating-type joints, which allow the link sections 114 to rotate about the joints 112. The rotating joints 112 provide the link sections 114 with a wide degree of angular freedom of movement. In one implementation, the robotic arm 116 is configured to provide displacement to the mechanical link 108 for translational movement. The movement range of the mechanical link 108 may be extended by the robotic arm 116 by appropriate movement, as will be apparent to those skilled in the art. In one implementation, the robotic arm 116 comprises a plurality of interconnected arm sections 120 cooperatively controlling the movement of the mechanical link 108.

Figure 2:
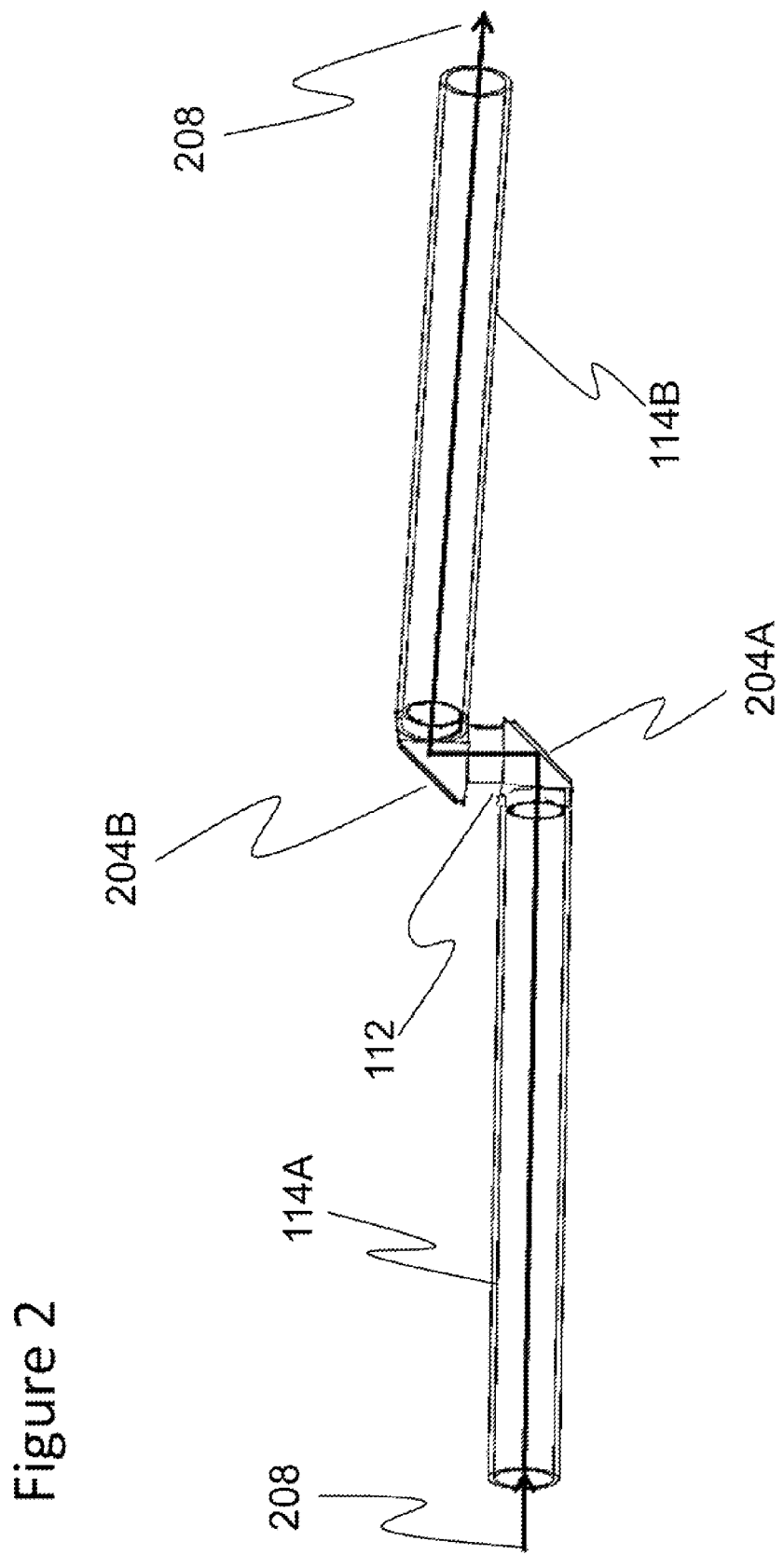
FIG. 2 illustrates two link sections coupled by a rotating joint.

FIG. 2 illustrates two link sections 114A and 114B coupled by a rotating joint 112. A pair of mirrors 204A and 204B is arranged in the rotating joint 112 to transfer the laser beam 208 between the pair of link sections 114A and 114B. The mirrors 204A and 204B are arranged in a manner to enable the transfer of the laser beam 208 regardless of the angular orientation of the link sections 114A and 114B. In one implementation, the link sections 114A and 114B are rigid tubes capable of transmitting a laser beam.

In one embodiment, a laser head assembly 124 is coupled to the mechanical link 108. The laser head assembly 124 is configured to receive the laser beam and to direct the laser beam to the object being tested. An optical scanner (not shown in FIG. 1) is mounted in the head assembly 124. The optical scanner may be a scanner mounted on a rotating axis proximate to the laser beam.

In one embodiment, a laser ultrasonic measurement system includes a first and a second laser source (not shown in FIG. 1) configured to generate a first and a second laser beam, respectively. The first laser source is coupled to the movable mechanical link 108, which directs the first laser beam to the object being tested. The second laser source is coupled to an optical link that directs the second laser beam to the object. In one implementation, the optical link is an optical fiber that is supported by the robot 110. Alternatively, the second laser source may be mounted in the head assembly 124 or on any part of robot 110 in a manner to allow the second laser beam to be directed to the object.

The first laser beam creates ultrasonic waves in the object while the second laser beam illuminates the object. It will be appreciated that part of the second laser beam is reflected by the object. The reflected beam is phase shifted by the ultrasonic waves in the object.

The reflected beam is received by an interferometer (not shown in FIG. 1), which is coupled to the optical scanner. The interferometer generates an ultrasonic signal responsive to the reflected beam. More precisely, the interferometer generates the ultrasonic signal responsive to the phase shift in the reflected beam.

Figure 3:
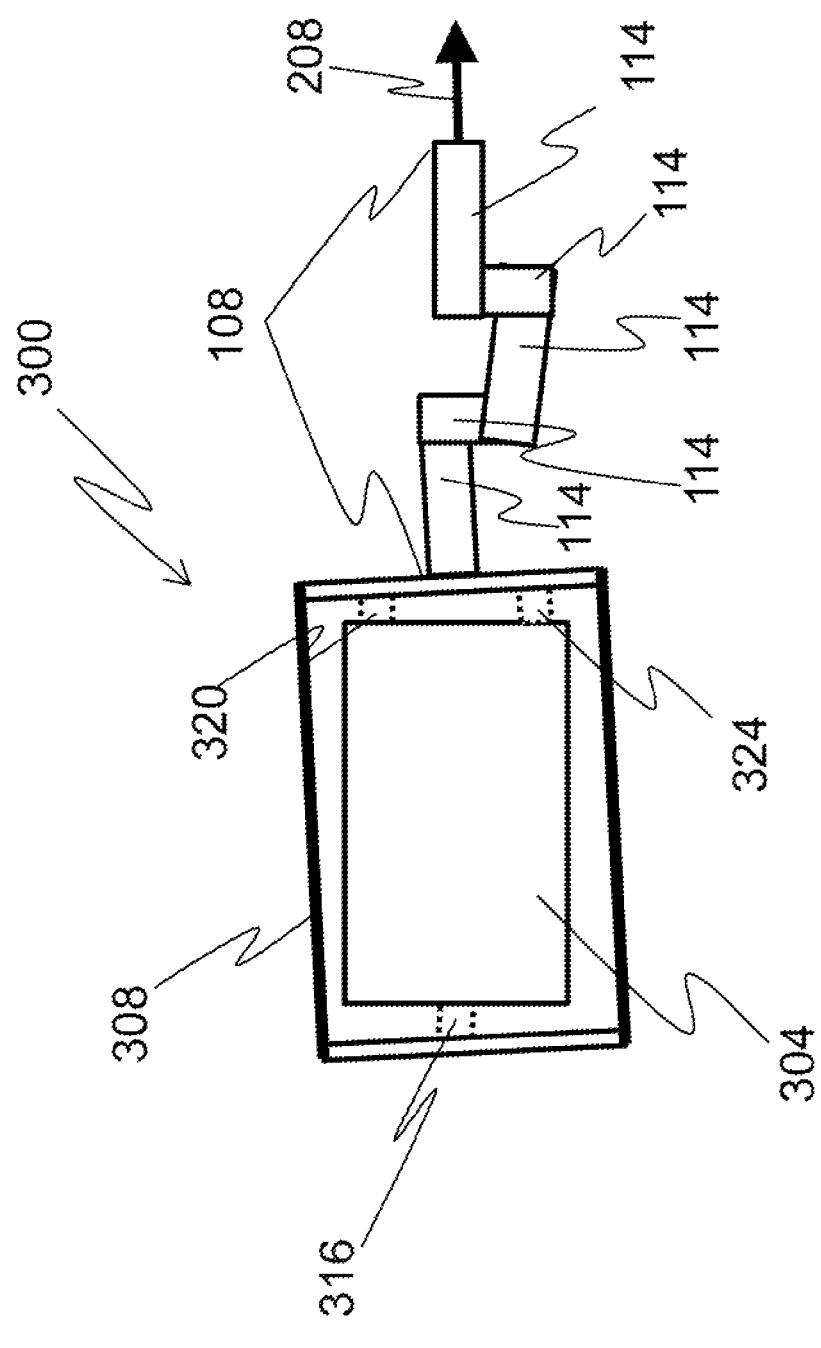
FIG. 3 illustrates an exemplary implementation of a laser source coupled to a movable mechanical link.

In one implementation, the laser source includes a resonator configured to generate a laser beam. FIG. 3 illustrates an exemplary implementation of a laser source 300 coupled to a movable mechanical link 108. The laser source 300 includes a resonator 308 configured to generate a laser beam from a lasing material. In one implementation, the resonator 308, for example, may include a gas vessel 304 containing a gaseous substance configured to generate a laser beam. One end of the mechanical link 108 is attached to the laser resonator 308 and aligned so that the laser beam can propagate through the full length of the mechanical link 108. Once aligned, the end of the mechanical link 108 is locked onto the laser resonator 308. The direction of propagation of a laser beam is defined by the resonator 308 position. The construction of the resonator 308 will be apparent to those skilled in the art.

Figure 4:
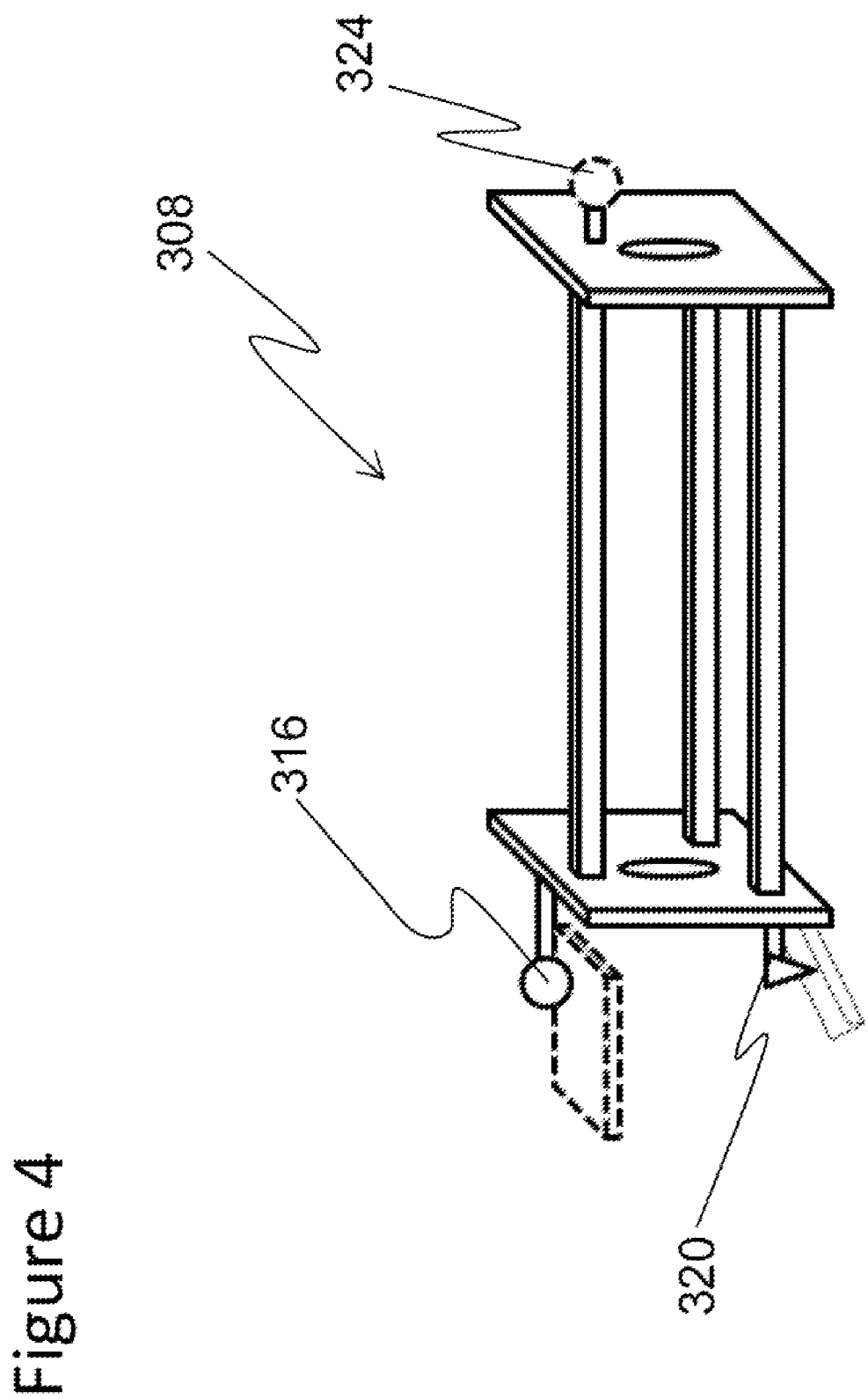
FIG. 4 illustrates a plane constraint, a line constraint and a point constraint.

The gas vessel 304 is mounted in an assembly or frame (not shown in FIG. 3). The resonator 308 is kinematically mounted on gas vessel 304 via a plurality of supports. In one implementation, the resonator 308 is kinematically mounted via supports 316, 320 and 324 to isolate from stress and deformation. For example, the support 316 may provide a plane constraint, the support 320 may provide a line constraint, while the support 324 may provide a point constraint, as illustrated in FIG. 4. The construction of the supports will be apparent to those skilled in the art. The plane, line and point constraints isolate the resonator 308 from stress and deformations, thereby enabling the laser beam to exit the resonator 308 at a fixed orientation relative to resonator 308. Because the mechanical link is aligned and locked in place relatively to the resonator 308, any movement of the resonator due to the gas vessel stress or deformation will maintain the laser beam alignment into the mechanical link.

In one implementation, the laser ultrasonic measurement system includes a first laser source and a second laser source, wherein the first laser source is a gas laser (e.g., CO2 laser) and the second laser source is a solid state laser or a fiber-type laser. The second laser source may be a hybrid laser built with solid state and fiber components. In one implementation, the second laser source is a stable low-power single-frequency laser amplified by one or more stages of amplification. The single-frequency laser and the amplification stages can be based on fiber laser technologies, solid-state laser technologies, flash-lamp technologies, or a combination of those technologies. The first laser (e.g., CO2 laser) generates a first laser beam used to create ultrasonic waves in the object being analyzed, while the second laser generates a second laser beam which illuminates the object. In one implementation, only the first laser source is kinematically mounted, as illustrated in FIG. 3.

Figure 5:
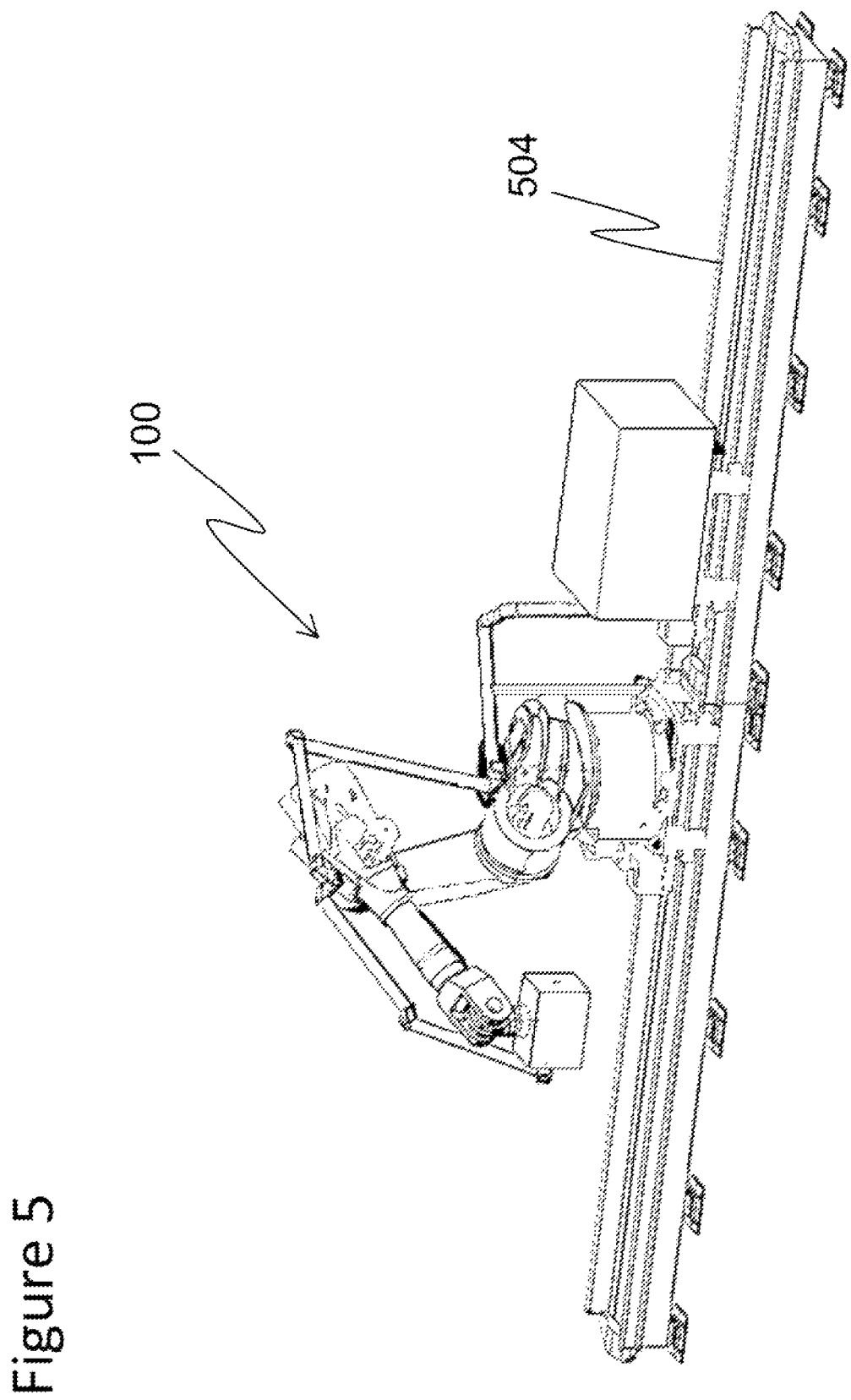
FIG. 5 shows the system of FIG. 1 mounted on a rail.
Figure 6:
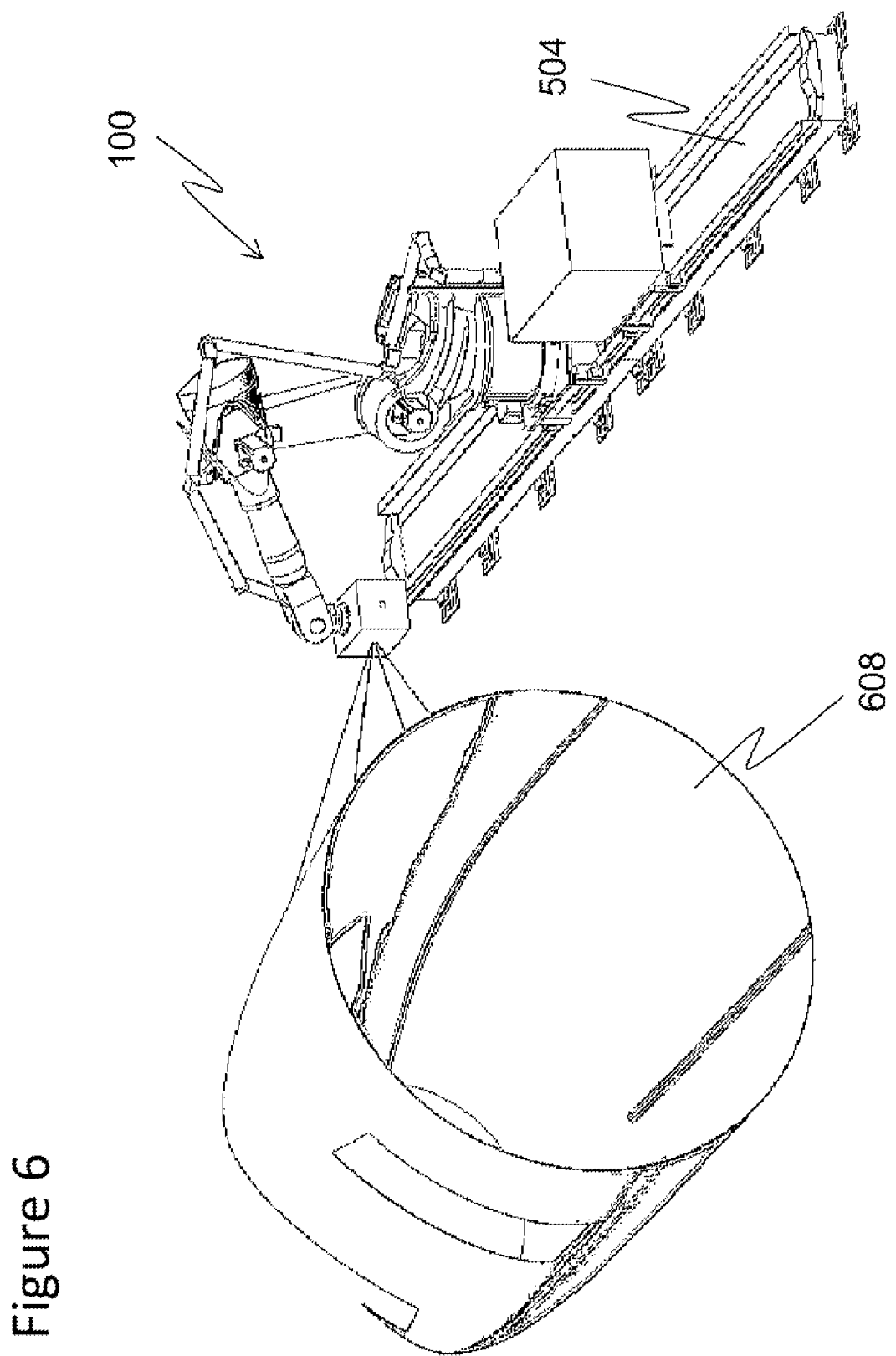
FIG. 6 shows the system of FIG. 1 conducting inspection of a structure.

FIG. 5 illustrates an implementation according to which the system 100 is mounted on a rail 504 to provide increased mobility. By mounting the system 100 on the rail 504, the total inspection range is significantly increased. FIG. 6 shows the system 100 mounted on the rail 504 conducting inspection of a structure 608.

Figure 7:
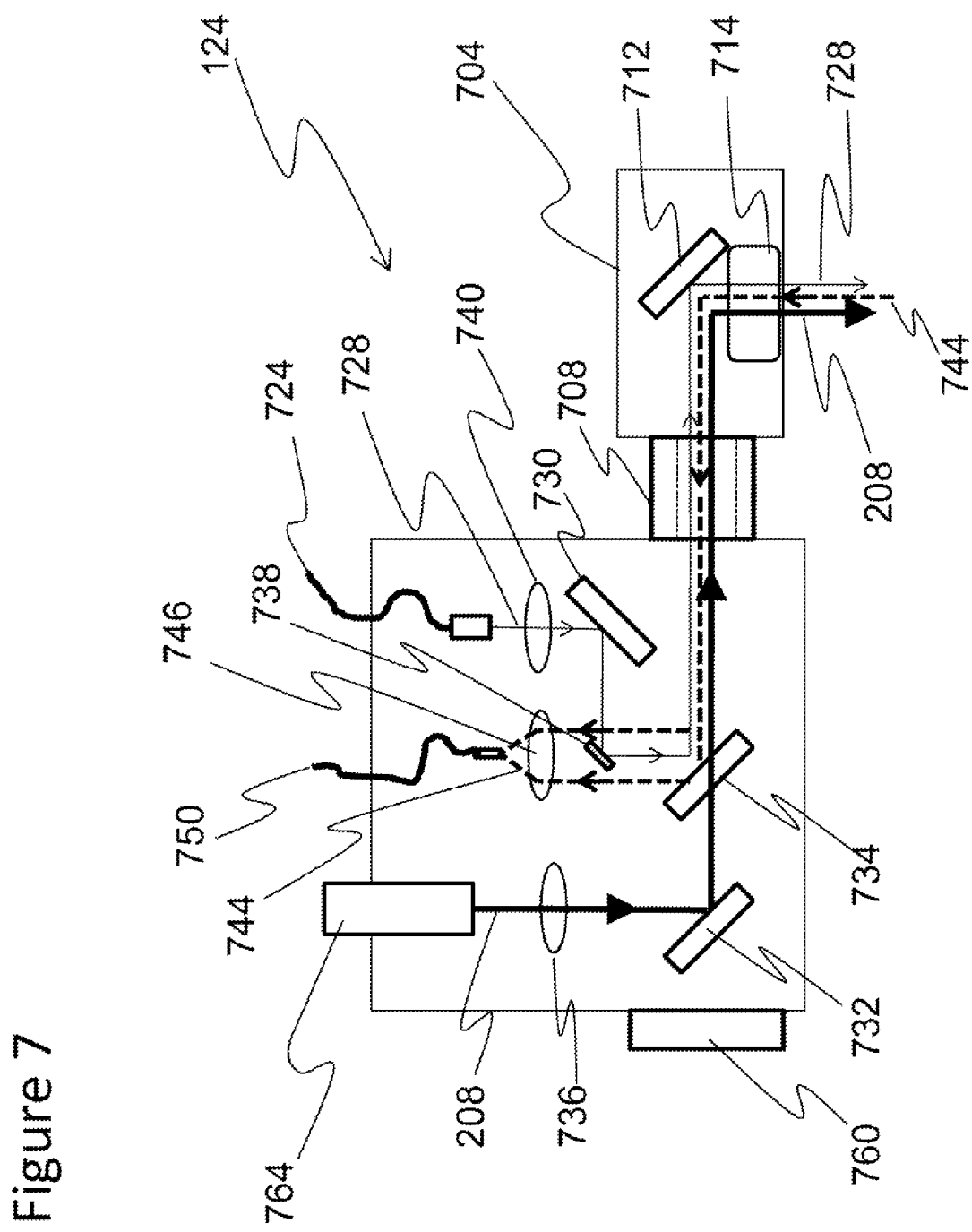
FIG. 7 illustrates a laser head assembly in accordance with one implementation.

FIG. 7 illustrates the laser head assembly 124 in accordance with one implementation. The laser head assembly 124 is attached to the robot arm 116 (not shown in FIG. 7) at attachment 760. One end of the mechanical link 108 (not shown in FIG. 7) is attached to the laser head 124 at attachment 764, transmitting the first laser beam 208 to the laser head 124. The second laser source (not shown in FIG. 7) is optically coupled to the laser head 124 through an optical fiber 724, transmitting a second laser beam 728 to laser head 124. The first and second laser beams 208 and 728 are optically coupled to an optical scanner 704 using optics and mirrors 730, 732, 734, 736, 738, and 740. The optical scanner 704 is mounted on a rotating axis 708, in which the rotation axis is concentric with the optical axis defined by laser beams 208 and 728. The optical scanner 704 aids in directing the laser beams 208 and 728 to an object being tested.

In one embodiment, the optical scanner includes two mirrors 712 and 714, each mounted on a galvanometer (not shown in FIG. 7) in a manner to direct the laser beams 208 and 728 onto the object. Light 744 from the second laser beam 728 reflected by the object is optically transmitted from the optical scanner 704 to an optical fiber 750 through optics and mirror 746 and 734. The mirror 738 is made small enough to allow reflected light 744 to reach optical fiber 750. An optical fiber 750 transmits reflected light 744 to an interferometer (not shown in FIG. 7). The interferometer is therefore optically coupled to the optical scanner through mirror 734, optics 746, and fiber 750.

It will also be appreciated that one or more of the elements depicted in the drawings/figures can also be implemented in a more separated or integrated manner, or even removed or rendered as inoperable in certain cases, as is useful in accordance with a particular application.

As used in the description herein and throughout the claims that follow, "a," "an" and "the" include plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in the following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed is:

1. A laser ultrasonic measurement system, comprising:
    a first and a second laser source configured to generate a first and a second laser beam, respectively;
    a robot configured to support and control the movement of at least a section of a moveable mechanical link to transmit the first laser beam to an object, the robot comprising a first movable arm section connected to a second movable arm section;
    a first movable mechanical link having a first end and a second end arranged to optically transmit the first laser beam from the first laser source to the second end of said first movable mechanical link, the first moveable mechanical link formed by a plurality of rigid sections interconnected by one or more rotating joints each containing a plurality of mirrors, the first movable arm section for the robot supporting the movement of the first movable mechanical link;
    an intermediate rotating joint containing a plurality of mirrors mechanically attached to the robot and optically connected to the second end of the first movable mechanical link and to a first end of a second movable mechanical link;
    the second movable mechanical link having a first end and a second end arranged to transmit the first laser beam from said intermediate rotating joint to the second end of the second movable mechanical link, the second movable mechanical link formed by a plurality of rigid sections interconnected by one or more rotating joints each containing a plurality of mirrors, said second movable arm section supporting the movement of said second movable mechanical link;
    an optical scanner proximate to the second end of said second movable mechanical link, an optical path for transmitting said second laser to said optical scanner;
    the optical scanner configured to direct the first and second laser beams onto the object; and
    an interferometer optically coupled to the optical scanner; the interferometer configured to receive reflected light from the object and in response generate an electrical signal.

2. The laser ultrasonic measurement system of claim 1, wherein said optical path for said second laser beam comprises an optical fiber.

3. The laser ultrasonic measurement system of claim 1, wherein the second laser source is placed proximate to the optical scanner.

4. The laser ultrasonic measurement system of claim 1, wherein the optical scanner is mounted on a rotating axis.

5. The laser ultrasonic measurement system of claim 1, wherein the first laser source is kinematically mounted in a housing assembly by a plurality of supports to isolate the laser source from stress.

6. The laser ultrasonic measurement system of claim 1, wherein the first laser source is a gas laser.

7. The laser ultrasonic measurement system of claim 1, wherein the first laser source is a CO2 laser.

8. The laser ultrasonic measurement system of claim 1, wherein the first laser source is a solid-state laser.

9. The laser ultrasonic measurement system of claim 1, wherein the second laser source is a solid-state laser or a fiber laser.

10. The laser ultrasonic measurement system of claim 1, wherein the second laser source is a hybrid laser.

11. The laser ultrasonic measurement system of claim 1, wherein the robot is mounted on a track for increased mobility.

12. A laser ultrasonic measurement system, comprising:
    a first and a second laser source configured to generate a first and a second laser beam, respectively;
    a robot comprising a first movable arm section connected to a second movable arm section;
    a first moveable mechanical link having first and second ends, the first movable mechanical link arranged to optically transmit the first laser beam from said first end to said second end, the mechanical link formed by a plurality of rigid sections interconnected by one or more rotating joints each joint containing a plurality of mirrors, the rigid sections of the first movable mechanical link supported by and movable with the first movable arm section of the robot;
    a second movable mechanical link having a first end and a second end, the second movable mechanical link arranged to optically transmit the first laser beam from said first end to said second end, the second mechanical link formed by a plurality of rigid sections interconnected by one or more rotating joints each containing a plurality of mirrors, the rigid sections of the second moveable mechanical link supported by and movable with the second movable arm section of the robot;
    an intermediate rotating joint containing a plurality of mirrors mechanically attached to the robot and optically connected to the second end of the first movable mechanical link and to the first end of the second movable mechanical link;

an optical scanner mounted for rotation proximate to the second end of said second movable mechanical link, the optical scanner configured to direct the first and second laser beams onto the object; and an interferometer optically coupled to the optical scanner; the interferometer configured to receive reflected light from the object and in response generate an electrical signal.

* * * * *